United States Patent
Martens et al.

(10) Patent No.: US 7,220,890 B2
(45) Date of Patent: May 22, 2007

(54) CHIMERIC MOUSE MODEL FOR ENDOMETRIOSIS

(75) Inventors: Mark G. Martens, Jenks, OK (US); Anil K. Kaul, Plymouth, MN (US); Rashmi Kaul, Plymouth, MN (US)

(73) Assignee: Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 10/296,066

(22) Filed: Nov. 13, 2002

(65) Prior Publication Data

US 2004/0031068 A1 Feb. 12, 2004

Related U.S. Application Data

(63) Continuation of application No. PCT/US00/06403, filed on Mar. 10, 2000.

(60) Provisional application No. 60/123,950, filed on Mar. 12, 1999.

(51) Int. Cl.
  *A01K 67/00* (2006.01)
  *A01K 67/033* (2006.01)
  *A61K 49/00* (2006.01)
  *A01N 63/00* (2006.01)
  *A01N 65/00* (2006.01)

(52) U.S. Cl. .......................... 800/9; 424/9.1; 424/9.2; 424/93.1

(58) Field of Classification Search .................... 800/3, 800/21, 14, 18, 9; 424/9.1, 9.2, 93.1
See application file for complete search history.

(56) References Cited

OTHER PUBLICATIONS

Vernon et al. "Experimental endometriosis in laboratory animals as a research model," Prog Clin Biol Res 323:49-60, 1990.*

Koujyo et al. "Induction of endometriosis and adenomyosis by transvaginal pituitary transplantation in mice with and without natural killer cell activity," Am J Reprod Immunol 40(6):441-6, 1998.*

Zamah et al. "Transplantation of normal and ectopic human endometrial tissue into athymic nude mice," Am J Obstet Gynecol 149(6):591-7, 1984.*

Bergqvist et al. "Human uterine endometrium and endometriotic tissue transplanted into nude mice," Am J Pathol 121:337-341, 1985.*

French et al. "Current and future prospects for xenotransplantation," Reprod Fertil Dev 10:683-696, 1998.*

D'Hooghe et al. "Clinical relevance of the baboon as a model for the study of endometriosis," Fertil Steril 68:613-625, 1997.*

Dizerega et al. "Endometriosis: role of ovarian steroids in initiation, maintenance, and suppression." Fertil Steril 33:649-653, 1980.*

Awwad, J T., et al., "The SCID mouse: an experimental model for endometriosis", *Human Reproduction*, vol. 14, No. 12, (1999),pp. 3107-3111.

Corwin, Elizabeth J., "Endometriosis: Pathophysiology, Diagnosis, and Treatment", *The Nurse Practitioner*, vol. 22, No. 10, (Oct. 1997).

D'Hooghe, T M., et al., "Immunobiology of Endometriosis", *Immunology of Reproduction, Blackwell Science*, In: Bronson RA, Alexander NJ, Anderson DJ, Branch DW, Kutteh WH, eds., (1996),322-356.

D'Hooghe, Thomas M., et al., "The effects of immunosuppression on development and progression of endometriosis in baboons (*Papio anubis*).", *Fertility Sterility*, vol. 64, No. 1, (Jul. 1995),pp. 172-178.

Halme, Jouko , et al., "Retrograde Menstruation in Healthy Women and in Patients With Endometriosis", *Obstet Gynecol.*, vol. 64, No. 2, (Aug. 1984),pp. 151-154.

Ishimaru, Tadayuki , et al., "Peritoneal Endometriosis: Endometrial Tissue Implantation as its Primary Etiologic Mechanism", *Am J Obstet Gynecol*, 165, (1991),pp. 210-214.

Klotz, M M., "Dysmenorrhea, Endometriosis, and Pelvic Pain", *Primary Care of Women. Norwalk: Appleton & Lange*, In: Lemcke DP, Pattison J, Marshall L, Cowley DS, eds.,(1995),426-428.

Oosterlynck, D J., et al., "Women with endometriosis show a defect in natural killer activity resulting in a decreased cytotoxicity to autologous endometrium", *Fertility and Sterility*, vol. 56., No. 1, (Jul. 1991),pp. 45-51.

Ramey, Jacques W., et al., "Inability to establish ectopic endometrium in a natural killer cell-deficient murine model. Immunologic, histologic and histochemical assessment", *The Journal of Reproductive Medicine*, vol. 41, No. 11, (Nov. 1996),807-814.

Ridley, John H., "The Histogenesis of Endometriosis—A Review of Facts and Fancies", *Obstetrical and Gynecological Survey*, vol. 20, No. 1, (1968),pp. 1-35.

Sampson, John A., et al., "Peritoneal Endometriosis Due To The Menstrual Dissemination of Endometrial Tissue Into The Peritoneal Cavity", *The Am Journal of Obstetrics and Gynecology*, vol. 4, (1927),pp. 422-469.

Steele, R W., et al., "Immunologic Aspects of Human Endometriosis", *Am Journal of Reprod Immuol.*, vol. 6, (1984),pp. 33-36.

Te Linde, Richard W., et al., "Experimental Endometriosis", *Am J Obstet Gynecol.*, vol. 60, No. 5, (1950),pp. 1147-1173.

Vernon, Michael W., et al., "Studies on the surgical induction of endometriosis in the rat", *Fertility and Sterility*, vol. 44, No. 5, (Nov. 1985),pp. 684694.

Vigano, Paola , et al., "Deficient antiendometrium lymphocyte-mediated cytotoxicity in patients with endometriosis", *Fertility and Sterility*, vol. 56, No. 5, (Nov. 1991),pp. 894899.

Aoki, Daisuke.,et al. ,"Successful heterotransplantation of human endometrium in SCID mice", *Obstetrics and Gynecology*, vol. 83, No. 2, (1994),220-228.

Bruner, Kaylon.L. ,et al. ,"Suppression of matrix metalloproteinases inhibits establishment of ectopic lesions by human endometrium in nude mice", *J. Clin. Invest.*, vol. 99, No. 12, (Jun. 15, 1997),2851-2857.

Koujyo, Tsunemaro.,et al. ,"Induction of endometriosis and adenomyosis by transvaginal pituitary transplantation in mice with and without natural killer cell activity", *Am. J. Reprod. Immunol.*, vol. 40, No. 6, (Dec. 1998),441-446.

\* cited by examiner

*Primary Examiner*—Thaian N. Ton
(74) *Attorney, Agent, or Firm*—Schwegman, Lundberg, Woessner & Kluth P.A.

(57) ABSTRACT

A non-human animal model for endometriosis is provided as well as methods of making and using the animal.

7 Claims, 4 Drawing Sheets

CHIMERIC MOUSE MODEL FOR ENDOMETRIOSIS

CROSS-REFERENCE TO RELATED APPLICATION

This application is a continuation of PCT/US00/06403, filed on Mar. 10, 2000, which claimed priority under 35 U.S.C. 119(e) of U.S. Provisional Application Ser. No.: 60/123,950, filed Mar. 12, 1999, which applications are incorporated herein by reference.

BACKGROUND OF THE INVENTION

Endometriosis is a chronic disease that affects nearly 5 million American women, or nearly 1 in 7 women of reproductive age (Klotz et al., 1995). Although endometriosis causes significant disability and distress in millions of women, it is often undiagnosed and, in general, is poorly understood (Corwin, 1997). Endometriosis is a benign disease that presents pleomorphic lesions of endometrial tissue containing glands or stroma or both growing at sites outside the uterine corpus. The ectopic sites include the ovaries, broad ligaments, rectovaginal septum, umbilicus, and laparotomy scars. The endometrial glands respond to hormonal stimuli, resulting in cyclic menstrual bleeding in the ectopic foci. Blood accumulates in cystic structures that are surrounded by inflammatory adhesions. Infertility, dysmenorrhea and chronic pelvic pain are the main symptoms, and are significant gynecological problems.

The exact etiology of this disease is controversial, but endometriosis occurs infrequently outside of the reproductive years, and appears to develop principally from the ectopic implantation of endometrial tissue entering the peritoneal space at the time of menstruation (Ishimaru et al., 1991; Sampson et al., 1927). Additionally, numerous experimental observations demonstrate that introduction of endometrial fragments into the peritoneal space of women (Ridley, 1968) and nonhuman primates (TeLinde et al., 1950) can result in the development of endometriosis.

Although retrograde menstruation has been reported in most women (Halme et al., 1984), endometriosis does not develop in all of them. Accumulating evidence suggests that altered cellular immunity may be involved in the pathogenesis of endometriosis both in women and in rhesus monkeys (Steele et al., 1984; Oosterlynck et al., 1991). Decreased in vitro lymphocyte proliferation in response to autologous endometrial cells has been reported in both rhesus monkeys and women with endometriosis (Steele et al., 1984). Decreased autologous antiendometrial lymphocytotoxicity and decreased natural killer (NK) cell activity has been reported in women with endometriosis when compared with women with a normal pelvis by some but not by other investigators (D'Hooghe et al., 1996).

There is evidence that immune surveillance is altered in women with endometriosis (Steele et al., 1984; Oosterlynck et al., 1991), which may facilitate the implantation of retrogradely shed menstrual endometrial cells. Whether immunosuppression facilitates the development of endometriosis is unknown. Immunosuppression has known profound effects on cellular and humoral immunity: global defects of T- and B-cell populations; decreased NK cell activity; 50% suppression of phytohemagglutinin-, concanavalin A-, and pokeweed mitogen-stimulated blastogenesis; decreased T-helper-T-suppressor ratio; impaired T-suppressor cell function; and reduced in vitro lymphokine-activated NK cell activity (D'Hooghe et al., 1996).

NK cell activity is decreased in women with endometriosis (Oosterlynck et al., 1991; Vigano et al., 1991). The reduced activity is not the result of a quantitative defect in these cells, nor does it appear to cause a significant reduction in systemic immunity (Oosterlynck et al., 1991; Vigano et al., 1991). The reduced NK cell activity may then result in a deficiency in the ability to reject autologous endometrial tissue, causing these women to have an increased risk for the development of endometriosis (Oosterlynck et al., 1991; Vigano et al., 1991).

Because of the expense and difficulties of human and primate research, models for the study of endometriosis have been developed in several other mammals. Many attempts have been made to elucidate the pathogenesis of endometriosis and to evaluate the therapeutic ability of new drugs against endometriosis by autotransplantation of endometrium to the peritoneal cavity of the subcutaneous layer in various laboratory animals, including rats (Klotz et al., 1995; Corwin, 1997; Ishimura et al., 1991), rabbits (Sampson, 1927; Ridley, 1968), monkeys (TeLinde et al., 1950; Halme et al., 1984) and mice (Aoki et al., 1994). The surgical transplantation of endometrial tissue wedges into the peritoneal sidewall and/or onto the ovary is the typical animal model used for studying endometriosis (Aoki et al., 1994; Vernon et al., 185; Zamah et al., 1984). This type of research model is helpful in investigating the effects of medications on ectopic endometrial tissue growth as well as in the in vivo pathophysiologic actions of these implants (Ramey et al., 1996).

The various existing animal models of endometriosis include the mouse (Yang and Foster, 1997), and the rat (Vernon and Wilson, 1985; Yang et al, 1996), where endometriosis is surgically induced by excising the uterine horn and uterine explants in ovariectomized rats and placed in anterior and posterior bifurcation of the uterine horns, and estrogen capsules implanted under the skin or exogenous hormone treatments. However, a major hurdle for understanding the etiology, pathophysiology and spontaneous evolution of the disease is the lack of an appropriate animal model closely mimicking human endometriosis.

Thus, what is needed is a non-human animal model for endometriosis.

SUMMARY OF THE INVENTION

The invention provides a mammalian chimera comprising a non-human mammal and human endometrial cells and/or tissue, as well as a method of preparing the chimeric mammal. The method comprises contacting, e.g., transplanting endometrial tissue and/or cells from a human to a non-human mammal so as to result in a non-human mammalian chimera. Preferably, the non-human mammal employed to prepare the chimera is immunodeficient, e.g., a severe combined immunodeficient (SCID) non-human mammal such as a SCID rat or mouse, or an athymic non-human mammal. The transplanted tissue is preferably from a human at risk of, or having, endometriosis. Also preferably, the endometrial tissue has (prior to contacting or transplanting) or yields (after contact or transplant) at least one endometritic lesion, at least one endometritic adhesion, proliferating human endometrial tissue, or any combination thereof. It is preferred that the endometrial tissues proliferates, forms at least one endometritic lesion, or at least one endometritic adhesion, in the absence of exogenously added hormone(s).

As described hereinbelow, immunodeficient SCID-beige, T, B and NK cell deficient mice were contacted, e.g., transplanted, with human endometrial tissue and/or cells so as to result in a non-human mammalian chimera. Ectopic or eutopic endometrial tissue may be obtained from patients with endometriotic lesions. The tissue is sectioned into uniform pieces and transplanted, for example, by stitching the tissue outside the left uterus horn, into female immunodeficient mice. Animals were then sacrificed after 12–24 weeks. The transplanted endometrial tissue was located in the abdominal cavity, with spread out adhesions. There was a correlation of the size of the endometrial cysts recovered from the chimeric animals with larger cysts observed in chimeric animals sacrificed at the end of 24 weeks compared to those sacrificed after 12 weeks. Endometrial graft from patient A induced endometriotic lesions in one out of two mice, however, both mice exhibited massive adhesions in the abdominal cavity. Tissue from patient B was successfully transplanted with endometriotic lesions in two out of two mice. Although tissue from patient C induced endometriotic lesion/proliferating endometrium in two of four mice, adhesions were present in all the animals. Tissue from patient D induced endometriosis in 3 of 4 mice. All the engrafted endometriotic cysts were stained with anti-human keratinin.

Thus, the chimeras of the invention were successfully transplanted with human endometriosis tissue, which formed proliferating endometriotic lesions in the chimeras that resemble human endometriosis. Therefore, the non-human mammalian chimeras of the invention may be useful to determine the role/effect of various hormones/therapeutic agents in treating human endometriosis, including the role of oral contraceptives on the natural history of endometriosis progression. In addition, co-transplantation of various human immune cells, such as T, B and macrophages from patients, may further define the role of immune cells in the pathophysiology of endometriosis.

Further provided is a method of using the mammalian chimera of the invention. The method comprises contacting the chimera with an agent. Then it is determined whether the agent inhibits, reduces or prevents the proliferation of human endometrial tissue, endometritic lesion formation, endometritic adhesion formation, or an combination thereof.

DETAILED DESCRIPTION OF THE INVENTION

Figure 1A:
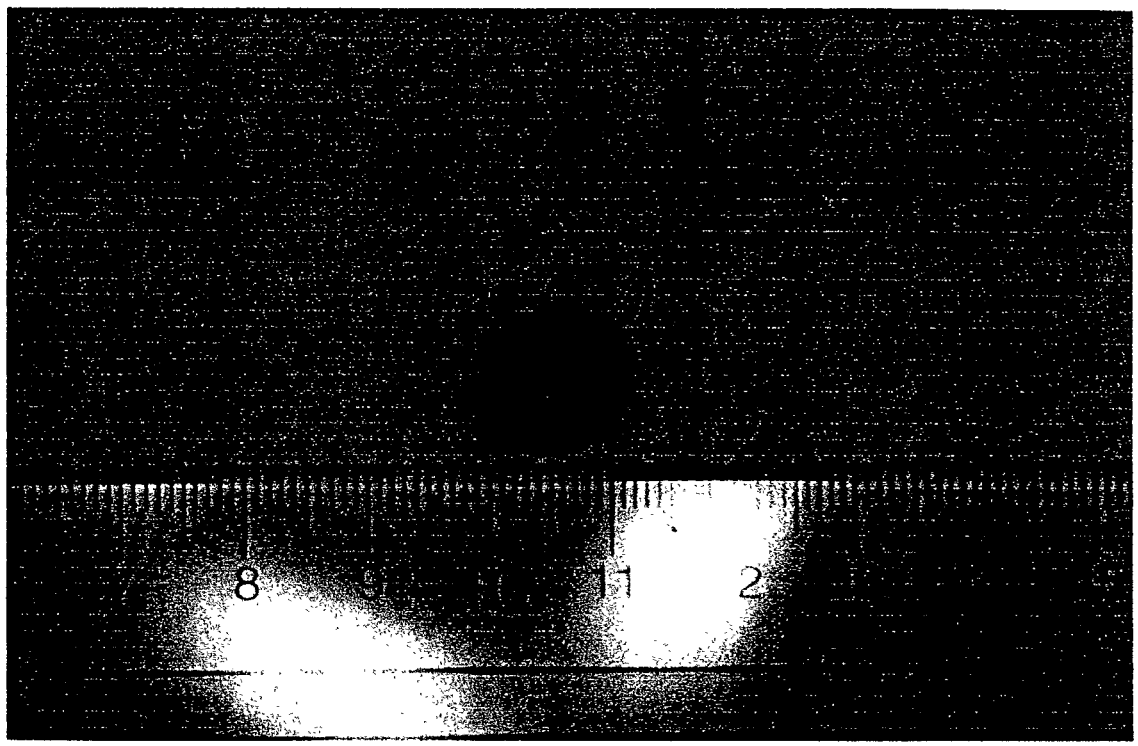
FIGS. 1A and B show endometritic tissue in the peritoneum of SCID mice transplanted with tissue from a human having endometriosis. Engrafted cysts were removed from the peritoneum and the mean diameter measured at 12 mm 24 weeks post-transplantation.

The present invention provides a non-human mammal useful as a model for endometriosis. Moreover, the non-human mammal of the invention is useful as a screening tool for agents that inhibit or prevent at least one symptom or characteristic of endometriosis.

The invention is further described by the following non-limiting example.

EXAMPLE 1

Materials and Methods

Patients. Samples of ectopic proliferative endometrial tissue were obtained from four patients with endometriosis at the time of diagnostic laparoscopy under an institutional review board approved protocol.

Animals. Female CB-17 SCID-beige mice were obtained from Taconic (Germantown, N.Y.). The mice were kept under specific pathogen-free conditions in AALAC accredited barrier facility and used between 5 and 8 wks of age. Induction procedure for the endometriosis was approved by the institutional animal care and use committee for this project.

Surgical Procedures for Experimental Model of Endometriosis. Endometrial explants obtained from endometriosis patients were cut into several pieces for transplanting into SCID mice. Mice were anesthetized under intraperitoneal anesthesia with 50 mg/kg of pentobarbital sodium.

A ventral incision along the left side was made. The endometrial explants, 2.5 to 3 mm square, were sutured outside the right uterine horn using 4.0 nylon suture. The muscle was closed with 4-0 Dexen II nylon suture and the skin was also closed with the same suture. The mice were given Buprenea in diluting water for the relief of pain, if any. All the mice tolerated the transplant very well with no graft versus host disease. The mice were sacrificed at three weeks or six weeks post transplantation by high anesthetizing doses and endometriotic sites were located in the abdomen. Severe adhesions were found in all the transplanted animals.

Following the location and measurement of the diameter of each endometriotic site, part of the sample was frozen for further investigation and part of it was fixed in 10% formalin and sent for histopathology and immunohistochemistry analysis.

Immunohistochemistry. Paraffin-embedded tissue sections were subjected to deparaffinization and rehydration prior to staining by preincubation for 20 minutes with 0.1% trypsin in PBS at 37° C. to expose antigenic sites. Endogenous peroxidase activity was then exhausted by incubation with 0.3% $H_2O_2$ in 96% methanol for 5 minutes. After rinsing in PBS, non-specific binding was blocked by incubation with normal goat serum ($\frac{1}{100}$ dilution in PBS) for 30 minutes. Sections were then kept overnight at 4° C. with a $\frac{1}{125}$ dilution of human pan cytokeratin antibody (rabbit polyclonal; BioGenex, San Ramon, Calif.). The sections were washed with PBS, then exposed sequentially to biotinylated secondary antibody (30 minutes), and avidin-biotinylated horseradish peroxidase complex (60 minutes) at room temperature (Vectastain Elite ABC detection system; Vector Laboratories, Burlingame, Calif.). Sections were then incubated with the peroxidase substrate 3.3' diaminobenzidine for 5 minutes to yield a brown reaction product, counterstained with haematoxylin for 5 minutes, rinsed in PBS and dipped in a lithium carbonate solution for 30 seconds. They were then dehydrated in ascending ethanol concentrations (70, 80, 95, and 100%) for 2 minutes each and coverslipped with Permount out of xylenes (Awwad et al., 1999).

Results

Figure 1B:
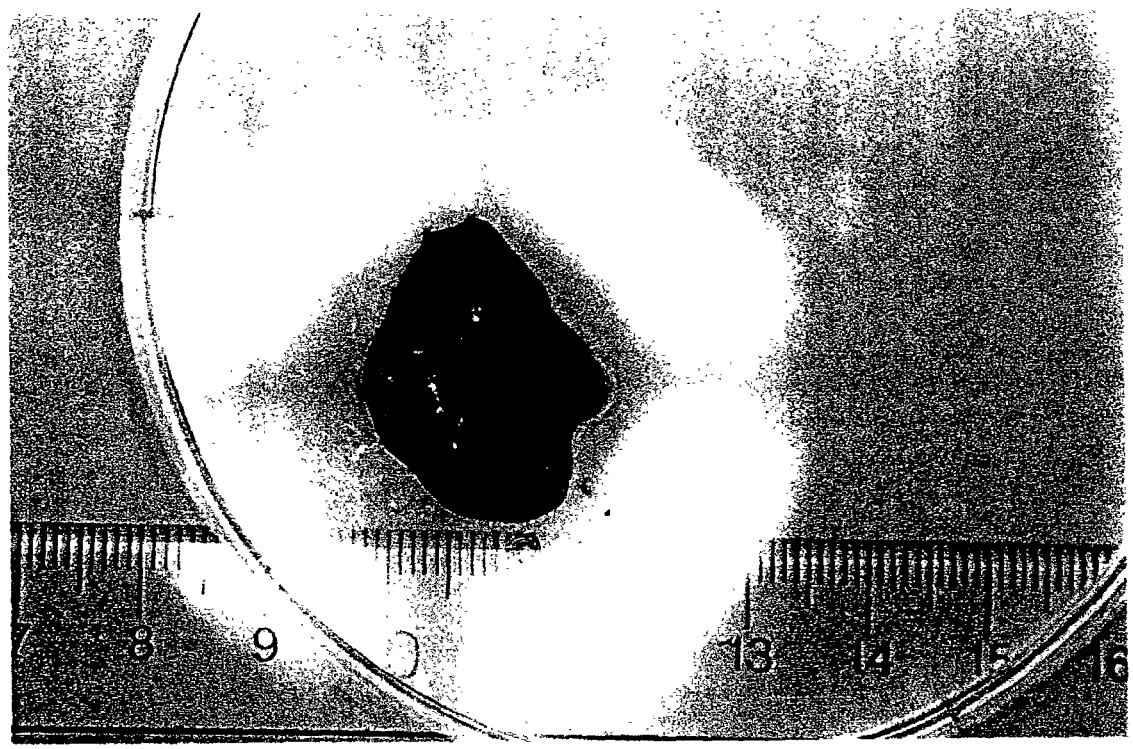

Success in forming an endometriosis cyst from one of the mice which was sacrificed 24 weeks post-transplantation is shown in FIGS. 1A and 1B. The transplantation of endometriosis endometrial grafts and induction of proliferating endometriotic lesions into SCID-beige mice was successful. Endometrial graft from patient A induced endometriotic lesion in one out of two mice, however, both mice exhibited massive adhesions in the abdominal cavity. Tissue from patient B was successfully transplanted with endoinetriotic lesions in two out of two mice. Although tissue from patient C induced endometriotic lesion/proliferating endometrium in two of four mice, adhesions were present in all the animals. Tissue from patient D induced endometriosis in 3 of 4 mice. All the engrafted endometriotic cysts were stained with anti-human keratin. Also, there was a correlation of the size of the endometrial cysts recovered from these animals with larger cysts observed in animals sacrificed at the end of 24 weeks compared to those sacrificed after 12 weeks. The visual examination of lesions removal from the peritoneum of recipient mice revealed endometriotic-like tissue with a white or reddish appearance (FIGS. 1A and 1B) firmly attached to underlying tissue 0. Mean endometriotic site diameter was 12 mm 24 weeks post transplantation. The mean number of implants per animal was 2–3.

Figure 2A:
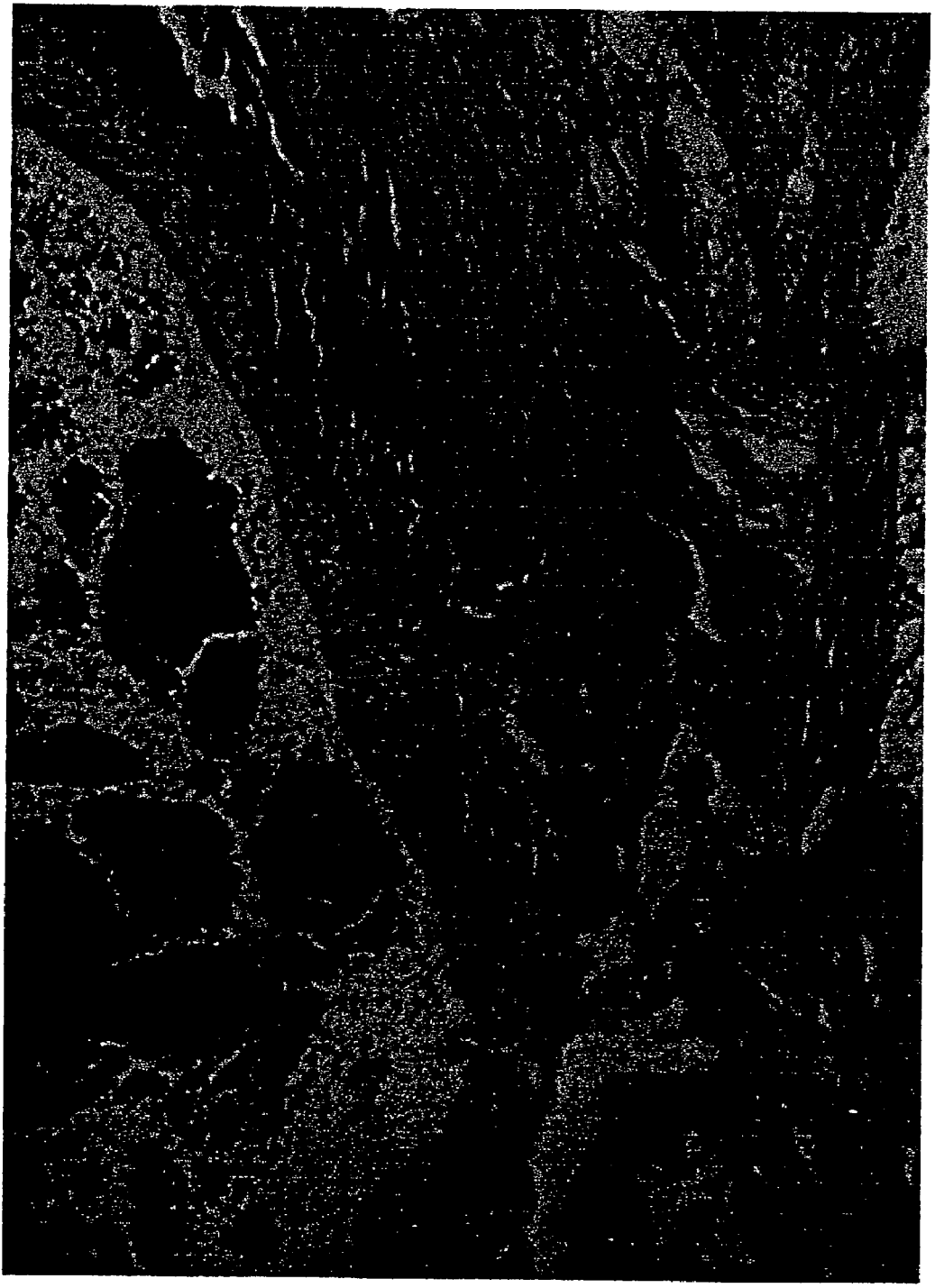
FIGS. 2A and B show the development of glands and stroma in cysts excised from SCID mice transplanted with tissue from a human having endometriosis. Histopathology of a cross-sectioned cyst showing actively growing endometrium with glands and stroma.
Figure 2B:

Apart from the cyst, there were several adhesions present around the area between lesions. Histology of endometriotic sites in the mouse were similar to the human endometriosis with glandular epithelium with adjacent stromal cell layer. Histopathological results of the cyst cross section determined actively growing proliferative endometrium with glands and stroma. These glands and stroma were at the same stage of development (FIGS. 2A and 2B). The endometrial lesions obtained from these mice were growing in either uterine smooth muscle or skeletal muscle or along with fat. Collagen like structures were seen in advanced endometriosis lesions.

In order to determine the distinct phylar and structural characteristics of ectopic endometrium glandular tissue, immunohistochemical staining with human pan-cytokeratin antibody was performed. Human and mouse endometrial epithelia served as positive and negative controls, respectively. Intense staining of the glandular lining was observed in all endometrial implants with distinct sparing of the surrounding stromal tissue. Human endometrial epithelium stained positively, while mouse endometrial epithelium invariably remained stain-free (Awwad et al., 1999).

Low natural killer activity in these SCID-beige mice may be a contributing factor for successful development of endometriosis in this model. This mouse model of endometriosis is unique in the development of lesion without any exogenous hormone treatment. The endometrial transplant in this model seems to thrive in response to the prostaglandin hormones produced by the explant itself as recent studies do indicate that endometriotic lesions may be capable of producing estrogens. Another possibility of hormone source may be the response to the available endogenous hormone cycle of the individual mouse.

Discussion

First, at the time of diagnosis, most patients with endometriosis have had the disease for an extended period, making it difficult to initiate any clinical experiments that would determine definitely the etiology or progression of the disease (Klotz et al., 1995). Second, it is difficult to carry out randomized studies with sufficient numbers of patients and meaningful controls, which obviates the need for multi-center-oriented research (Corwin, 1997).

An important reason for the lack of progress in endometriosis research is study design; very few studies have been carried out so far using adequate control groups. When symptomatic patients with endometriosis are compared with women with a normal pelvis, adenomyosis, leimyomas, adhesions, or other pelvic pathology, two factors usually are studied in a combined way: the pelvic condition (presence of endometriosis or other pathology) and symptoms (none, infertility, pain, and other symptoms).

A causal relation between endometriosis and infertility has not been established definitely. In women with moderate to severe endometriosis, pelvic adhesions may cause impairment of tuboovarian function and infertility. An inverse relation between pregnancy rates (PRs) and the degree of endometriosis often has been proposed, but this has not been substantiated in prospectively controlled fertility trials.

It is possible that a longer period without conception is required for the development of ovarian or deep endometriosis than for peritoneal endometriotic lesions. It also is possible that ovarian endometriotic cysts may have a different pathogenesis than peritoneal endometriosis. This hypothesis is supported by the observation that ovarian endometriosis could not be induced experimentally by seeding or injecting menstrual endometrium on top of or beneath the ovarian capsule, respectively, and that large endometriotic cysts were observed only in an immunosuppressed baboon.

Experimental induction of endometriosis offers the opportunity to make serial observations in the same animal before and after induction, enabling investigators to identify factors, e.g., growth factors, cytokines, and integrins, in peripheral blood (PB), peritoneal fluid (PF) and other physiological fluids and tissue, that are the consequence of, or promote, endometriosis. The identification of specific growth factors, cytokines, and/or integrins that are associated with endometriosis or progression thereof may explain why endometriosis can be induced more successfully with menstrual endometrium than with luteal endometrium. Moreover, the methods of the invention are useful to determine whether non-pathologic uterine endometrial cells or endometrial cells from a non-uterine source, e.g., endometrial cells in PF, and from a certain stage in the menstrual cycle, can be implanted to a non-human mammal. Further, as baboons with experimental endometriosis often had advanced stages of disease, larger non-human mammals may offer yet further models for the study of medical and/or surgical treatment of this disease.

REFERENCES

Aoki D, Katsuki Y, Shimizu A, Kakinuma C, Nozawa S. Successful heterotransplantation of human endometrium in SCID mice. *Obstet Gynecol,* 83, 220 (1994).

Awwad J T, Sayegh R A, Tao X J, Hassan T, Awwad S T, Isaacson K. The SCID mouse: an experimental model for endometriosis. *Human Reprod,* 14, 3107 (1999).

Corwin, E J. Endometriosis: pathophysiology, diagnosis, and treatment. *The Nurse Practitioner,* 22, 35 (1997).

D'Hooghe T M, Hill J A. Immunobiology of endometriosis. In: Bronson R A, Alexander N J, Anderson D J, Branch D W, Kutteh W H, eds. *Immunology of Reproduction. Blackwell Science,* 322 (1996).

D'Hooghe T M, Bambra C S, Raeymaekers B M, Hill J A, Koninckx P R. Immunosuppression can increase progression of spontaneous endometriosis in baboons. *Fertil Steril,* 64, 172 (1995).

Halme J, Becker S, Hammond M G, Raj S G, Talbert L M. Retrograde menstruation in healthy women and in patients with endometriosis. *Obstet Gynecol,* 1,151 (1984).

Ishimaru T, Masuzaki H. Peritoneal endometriosis: endometrial tissue implantation as a primary etiologic mechanism. *Am J Obstet Gynecol*, 165, 210 (1991).

Klotz M M. Dysmenorrhea, endometriosis, and pelvic pain. In: Lemcke D P, Pattison J, Marshall L, Cowley D S, eds. Primary Care of Women. Norwalk: Appleton & Lange, 1995:26.

Oosterlynck D J, Camille F S, Waer M, Vandeputte M, Koninckx P R. Women with endometriosis show a defect in natural killer activity resulting in a decreased cytotoxicity to autologous endometrium. *Fertil Steril*, 56, 45 (1991).

Ramey J W, Booker S S, Kanbour-Shakir A, Campbell A E, Sharpe-Timms K L, Archer D F. Inability to establish ectopic endometrium in a natural killer cell-deficient murine model. *J Reprod Med*, 41, 807 (1996).

Ridley J H. The histogenesis of endometriosis. A review of facts and fancies. *Obstet Gynecol Surv*, 20, 1 (1968).

Sampson J A. Peritoneal endometriosis due to menstnial dissemination of endometrial tissue tissues into the peritoneal cavity. *Am J Obstet Gynecol*, 4, 422 (1927).

Steele R W, Dmowski W P, Marmet D J. Immunologic aspects of endometriosis. *Am J Reprod immunol*, 6, 33 (1984).

TeLinde R W, Scott R B. Experimental endometriosis. *Am J Obstet Gynecol*, 60, 1147 (1950).

Vernon M W, Wilson E A. Studies on the surgical induction of endometriosis in the rat. *Fertil Steril*, 44, 684 (1985).

Vigano P, Vercelline P, diBlasio A M, et al. Deficient antiendometrium lymphocytemediated cytotoxicity in patients with endometriosis. *Fertil Steril*, 56, 894 (1991).

Zamah N M, Dodson M G, Stephens L C, Buttram V C, Besch P K, Kaufman R H. Transplantation of normal and ectopic human endometrial tissue into athymic nude mice. *Am J Obstet Gynecol*, 149, 591 (1984).

While the present invention has been described in connection with the preferred embodiment thereof, it will be understood many modifications will be readily apparent to those skilled in the art, and this application is intended to cover any adaptations or variations thereof. It is manifestly intended this invention be limited only by the claims and equivalents thereof.

What is claimed is:

1. A chimeric mouse, which is a model for endometriosis, wherein said chimeric mouse is an immunocompromised mouse comprising ectopic human endometrial cells or tissue, wherein the ectopic cells or tissue are affixed to the outside of the uterine horn of the immunocompromised mouse, and wherein the ectopic cells or tissue proliferate, form at least one endometrial lesion, form at least one endometrial adhesion, or any combination thereof, and wherein the chimeric mouse is not subjected to exogenous hormone treatment.

2. The chimeric mouse of claim 1 wherein the human endometrial tissue is from a human with endometriosis.

3. The chimeric mouse of claim 1 wherein the human endometrial cells or tissue are obtained during a diagnostic procedure.

4. A method of preparing the chimeric mouse, which is a model for endometriosis, of claim 1, comprising:

introducing to an immunocompromised mouse, ectopic human endometrial cells or tissue under conditions effective to result in a chimeic mouse comprising proliferating human endometrial cells or tissue, at least one human endometrial lesion, at least one human endometrial adhesion, or any combination thereon wherein the ectopic cells or tissue are affixed to the outside of the uterine horn of the immunocompromised mouse, and wherein the chimeric mouse is not subjected to exogenous hormone treatment.

5. A method of using a chimeric mouse model for endometriosis, comprising:

(a) administering an agent to the chimeric mouse of claim 1; and (b) determining whether the agent reduces or inhibits at least one characteristic of endometriosis relative to a corresponding chimeric mouse which has not been administered the agent.

6. The method of claim 5 wherein the immunocompromised mouse is not subjected to exogenous hormone treatment.

7. The method of claim 4, wherein the immunocompromised mouse is not subjected to exogenous hormone treatment.

* * * * *